(12) United States Patent
Zuo et al.

(10) Patent No.: US 10,228,325 B2
(45) Date of Patent: Mar. 12, 2019

(54) DOWNHOLE FLUID ANALYSIS METHOD AND APPARATUS FOR DETERMINING VISCOSITY

(71) Applicant: Schlumberger Technology Corporation, Sugar Land, TX (US)

(72) Inventors: Youxiang Zuo, Burnaby (CA); Hadrien Dumont, Houston, TX (US); Richard Jackson, Cape Town (ZA); Ilaria De Santo, Paris (FR); Oliver C. Mullins, Houston, TX (US); Cosan Ayan, Istanbul (TR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/027,227

(22) PCT Filed: Oct. 3, 2014

(86) PCT No.: PCT/US2014/058977
§ 371 (c)(1),
(2) Date: Apr. 4, 2016

(87) PCT Pub. No.: WO2015/051220
PCT Pub. Date: Apr. 9, 2015

(65) Prior Publication Data
US 2016/0252454 A1 Sep. 1, 2016

Related U.S. Application Data

(60) Provisional application No. 61/887,125, filed on Oct. 4, 2013.

(51) Int. Cl.
*G01N 21/59* (2006.01)
*E21B 49/08* (2006.01)
(Continued)

(52) U.S. Cl.
CPC ......... *G01N 21/5907* (2013.01); *E21B 49/08* (2013.01); *E21B 49/10* (2013.01);
(Continued)

(58) Field of Classification Search
CPC .... G01N 33/2823; G01N 11/00; G01N 11/02; G01N 2011/008; G01N 21/5907;
(Continued)

(56) References Cited

U.S. PATENT DOCUMENTS 4,994,671 A 2/1991 Safinya et al.
5,331,156 A 7/1994 Hines et al.
(Continued)

FOREIGN PATENT DOCUMENTS

CA 2638949 A1 2/2010
WO 2011007268 A1 1/2011
(Continued)

OTHER PUBLICATIONS

International Search Report and the Written Opinion for International Application No. PCT/US2014/058977 dated Jan. 20, 2015.
(Continued)

*Primary Examiner* — David Porta
*Assistant Examiner* — Blake Riddick
(74) *Attorney, Agent, or Firm* — Michael Dae (57) ABSTRACT

The present disclosure relates to a downhole fluid analysis method that includes withdrawing formation fluid into a downhole tool at a plurality of stations within a wellbore, analyzing the formation fluid within a fluid analyzer of a downhole tool to determine properties of the formation fluid for the plurality of stations, and developing, based on the determined properties of the formation fluid, a relationship for predicting viscosity from a measured optical density.

13 Claims, 6 Drawing Sheets

(51) Int. Cl.
*E21B 49/10* (2006.01)
*G01N 11/00* (2006.01)
*G01N 11/02* (2006.01)
*G01N 30/88* (2006.01)

(52) U.S. Cl.
CPC .............. *G01N 11/00* (2013.01); *G01N 11/02* (2013.01); *G01N 30/88* (2013.01); *E21B 2049/085* (2013.01); *G01N 2011/008* (2013.01)

(58) Field of Classification Search
CPC ......... G01N 30/88; E21B 49/08; E21B 49/10; E21B 2049/085
USPC ....... 250/255, 256, 343, 253, 254; 702/6, 11
See application file for complete search history.

(56) References Cited

U.S. PATENT DOCUMENTS

| | | | |
|---|---|---|---|
| 6,178,815 B1* | 1/2001 | Felling | E21B 49/10 166/250.07 |
| 6,476,384 B1 | 11/2002 | Mullins et al. | |
| 7,526,953 B2 | 5/2009 | Goodwin et al. | |
| 7,822,554 B2 | 10/2010 | Zuo et al. | |
| 7,920,970 B2 | 4/2011 | Zuo et al. | |
| 7,996,154 B2 | 8/2011 | Zuo et al. | |
| 8,271,248 B2 | 9/2012 | Pomerantz et al. | |
| 8,434,356 B2 | 5/2013 | Hsu et al. | |
| 2003/0176973 A1* | 9/2003 | Hashem | E21B 49/08 702/13 |
| 2005/0242807 A1 | 11/2005 | Freedman | |
| 2007/0143023 A1* | 6/2007 | Betancourt | E21B 49/08 702/11 |
| 2009/0312997 A1 | 12/2009 | Freed et al. | |
| 2009/0316528 A1* | 12/2009 | Ramshaw | E21B 44/00 367/83 |
| 2010/0043538 A1 | 2/2010 | Cheng et al. | |
| 2011/0042070 A1* | 2/2011 | Hsu | E21B 47/102 166/250.01 |
| 2011/0246143 A1 | 10/2011 | Pomerantz et al. | |
| 2012/0232799 A1* | 9/2012 | Zuo | E21B 49/00 702/6 |
| 2013/0112406 A1 | 5/2013 | Zuo et al. | |

FOREIGN PATENT DOCUMENTS

| | | |
|---|---|---|
| WO | 2012042397 A2 | 4/2012 |
| WO | 2013015957 A1 | 1/2013 |
| WO | 2015051220 A1 | 4/2015 |

OTHER PUBLICATIONS

Reyadh A. Almehaideb et al., "EOS tuning to model full field crude oil properties using multiple well fluid PVT analysis," Journal of Petroleum Science and Engineering, vol. 26, Issues 1-4, pp. 291-300, (2000).

H.J. Ng et al., "The Measurement and Prediction of Hydrate Formation in Liquid Hydrocarbon-Water Systems," Industrial& Engineering Chemistry Fundamentals, vol. 15, pp. 293-298 (1976).

H.J. Ng et al., "Hydrate Formation in Systems Containing Methane, Ethane, Propane, Carbon Dioxide or Hydrogen Sulfide in the Presence of Methanol," Fluid Phase Equilibria, vol. 21, pp. 145-155 (1985).

H.J. Ng et al., "New Developments in the Measurement and Prediction of Hydrate Formation for Processing Needs," International Conference on Natural Gas Hydrates, Annals of the New York Academy of Sciences, vol. 715, 450-462 (1994).

J.Y. Zuo et al. "Representation of Hydrate Phase Equilibria in Aqueous Solutions of Methanol and Electrolytes Using an Equation of State," Energy and Fuels, 14, 19-24 (2000).

J.Y. Zuo et al., "A Thermodynamic Model for Gas Hydrates in the Presence of Salts and Methanol," Chemical Engineering Communications, 184, 175-192 (2001).

J.Y. Zuo et al., "An improved thermodynamic model for wax precipitation from petroleum fluids," Chemical Engineering Science, vol. 56, 6941-6947 (2001).

J.Y. Zuo et al., "Wax Formation from Synthetic Oil Systems and Reservoir Fluids," Energy & Fuels, 2008, 22, 2390-2395.

J. Du et al., "A Thermodynamic Model for the Predictions of Asphaltene Precipitation," Petroleum Science and Technology, 22, 1023 (2004).

Mok, M.M., Liu, X., Bai, Z., Lei, Y., Lodge, T.P. "Effect of Concentration on the Glass Transition and Viscoelastic Properties of Poly(methyl methacrylate)/Ionic Liquid Solutions", Macromolecules, 44, 1016-1025 (2011).

Mullins, O. C. The Modified Yen Model. Energy & Fuels 2010, 24(4), 2179-2207.

Freed, D. E.; Mullins, O. C.; Zuo, J. Y. Theoretical Treatment of Asphaltenes in the Presence of GOR Gradients. Energy & Fuels 2010, 24(7), 3942-3949.

Zuo, J. Y.; Mullins, O. C.; Freed, D.; Zhang, D.; Dong, C.; Zeng, H. Analysis of Downhole Asphaltene Gradients in Oil Reservoirs with a New Bimodal Asphaltene Distribution Function. Journal of Chem. Eng. Data 2011, 56(4), 1047-1058.

Khan, S. A.; Al-Marhoun, M. A.; Duffuaa, S. O.; Abu-Khamsin, S. A. Viscosity Correlations for Saudi Arabian Crude Oils. SPE Paper 15720 presented at the Fifth SPE Middle East Conference held in Manama, Bahrain, Mar. 7-10, 1987.

Zuo, J.Y., Mullins, O.C., Garcia, G., Dong, C., Dubost, F.X., Zhang, D., Jia, N., Ayan, C., "Viscosity and Asphaltene Profiles in Mobile Heavy Oil Reservoirs", WHOC12-184, presented and published in the proceedings for the 2012 World Heavy Oil Congress, Aberdeen, UK, Sep. 10-13, 2012.

International Preliminary Report on Patentability issued in the related PCT application PCT/US2014/058977, dated Apr. 5, 2016 (9 pages).

\* cited by examiner

DOWNHOLE FLUID ANALYSIS METHOD AND APPARATUS FOR DETERMINING VISCOSITY

CROSS-REFERENCE TO RELATED APPLICATION

This application claims priority to U.S. Provisional Patent Application Ser. No. 61/887,125 filed on Oct. 4, 2013 and entitled, "Downhole Fluid Analysis Method and Apparatus for Determining Viscosity," the contents of which are incorporated by reference herein for all purposes.

BACKGROUND OF THE DISCLOSURE

Wellbores (also known as boreholes) are drilled to penetrate subterranean formations for hydrocarbon prospecting and production. During drilling operations, evaluations may be performed of the subterranean formation for various purposes, such as to locate hydrocarbon-producing formations and manage the production of hydrocarbons from these formations. To conduct formation evaluations, the drill string may include one or more drilling tools that test and/or sample the surrounding formation, or the drill string may be removed from the wellbore, and a wireline tool may be deployed into the wellbore to test and/or sample the formation. These drilling tools and wireline tools, as well as other wellbore tools conveyed on coiled tubing, drill pipe, casing or other conveyers, are also referred to herein as "downhole tools."

Formation evaluation may involve drawing fluid from the formation into a downhole tool for testing and/or sampling. Various devices, such as probes and/or packers, may be extended from the downhole tool to isolate a region of the wellbore wall, and thereby establish fluid communication with the subterranean formation surrounding the wellbore. Fluid may then be drawn into the downhole tool using the probe and/or packer. Within the downhole tool, the fluid may be directed to one or more fluid analyzers and sensors that may be employed to detect properties of the fluid while the downhole tool is stationary within the wellbore. The properties of the fluid may be employed to determine reservoir architecture, connectivity, and compositional gradients, among others.

SUMMARY

The present disclosure relates to a downhole fluid analysis method that includes withdrawing formation fluid into a downhole tool at a plurality of stations within a wellbore, analyzing the formation fluid within a fluid analyzer of a downhole tool to determine properties of the formation fluid for the plurality of stations, and developing, based on the determined properties of the formation fluid, a relationship for predicting viscosity from a measured optical density.

The present disclosure also relates to a downhole tool that includes a fluid analyzer to determine properties of formation fluid for a plurality of stations within a wellbore, and a controller. The controller is designed to execute instructions stored within the downhole tool to determine whether clusters exist within the formation fluid based on the determined properties and to develop, based on the determined properties of the formation fluid, a relationship for predicting viscosity from a measured optical density.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the present disclosure provides many different embodiments, or examples, for implementing different features of various embodiments. Specific examples of components and arrangements are described below to simplify the present disclosure. These are, of course, merely examples and are not intended to be limiting.

The present disclosure relates to methods for determining viscosities of downhole fluids using fluid composition data obtained by the downhole tool. According to certain embodiments, the viscosities may be determined in substantially real-time as formation fluid is directed through a fluid analyzer of the downhole tool. In certain embodiments, the type of the fluid, such as heavy oil, black oil, and light oil may be determined downhole based on asphaltene concentrations and used to select a method for determining the viscosity of the fluid. The selected method may then be employed while the tool is downhole to estimate the viscosity of the fluid using optical density measurements. In one example, the viscosity of the fluid also may be measured by a viscosity sensor. The measured viscosity may be compared to the estimated viscosity to detect changes in reservoir architecture.

Figure 1:
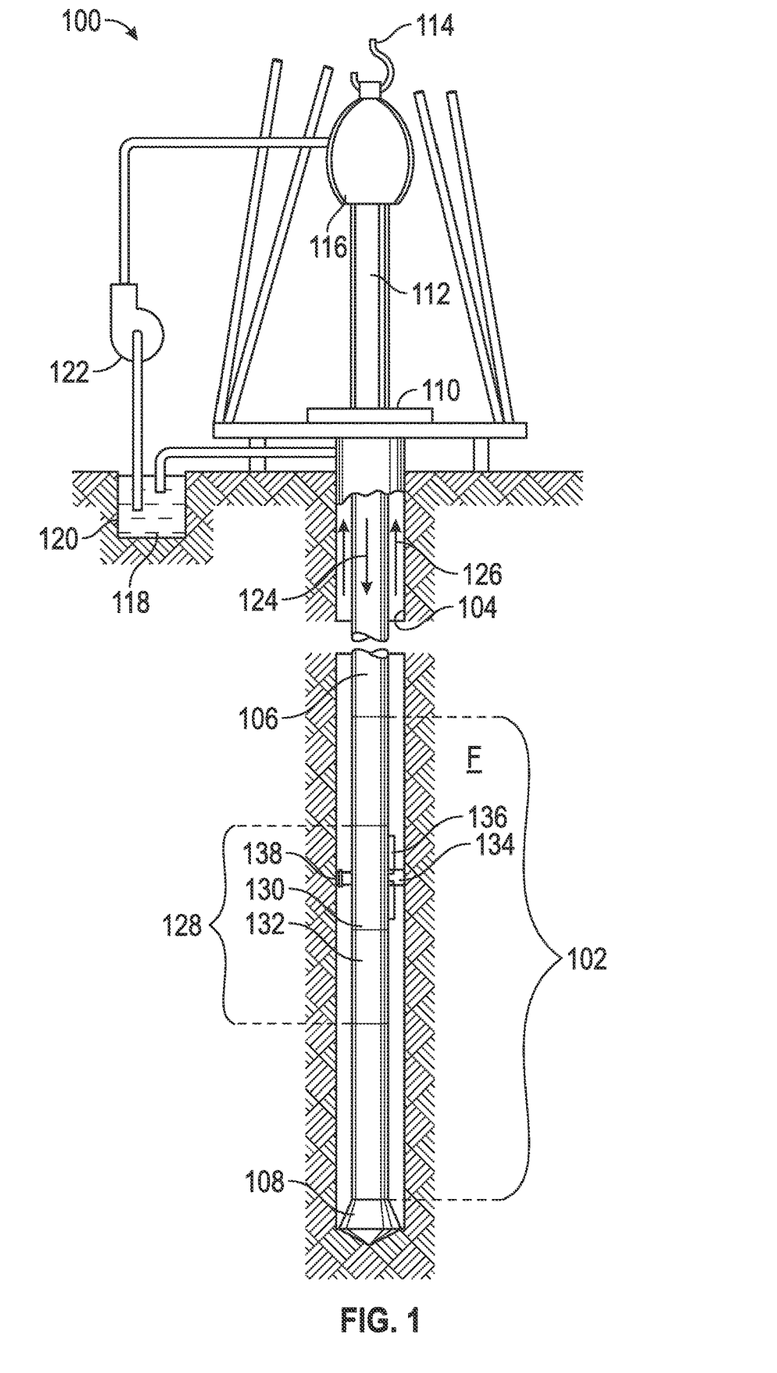
FIG. 1 is a schematic view of an embodiment of a wellsite system that may employ downhole fluid analysis methods for determining viscosity, according to aspects of the present disclosure.
Figure 2:
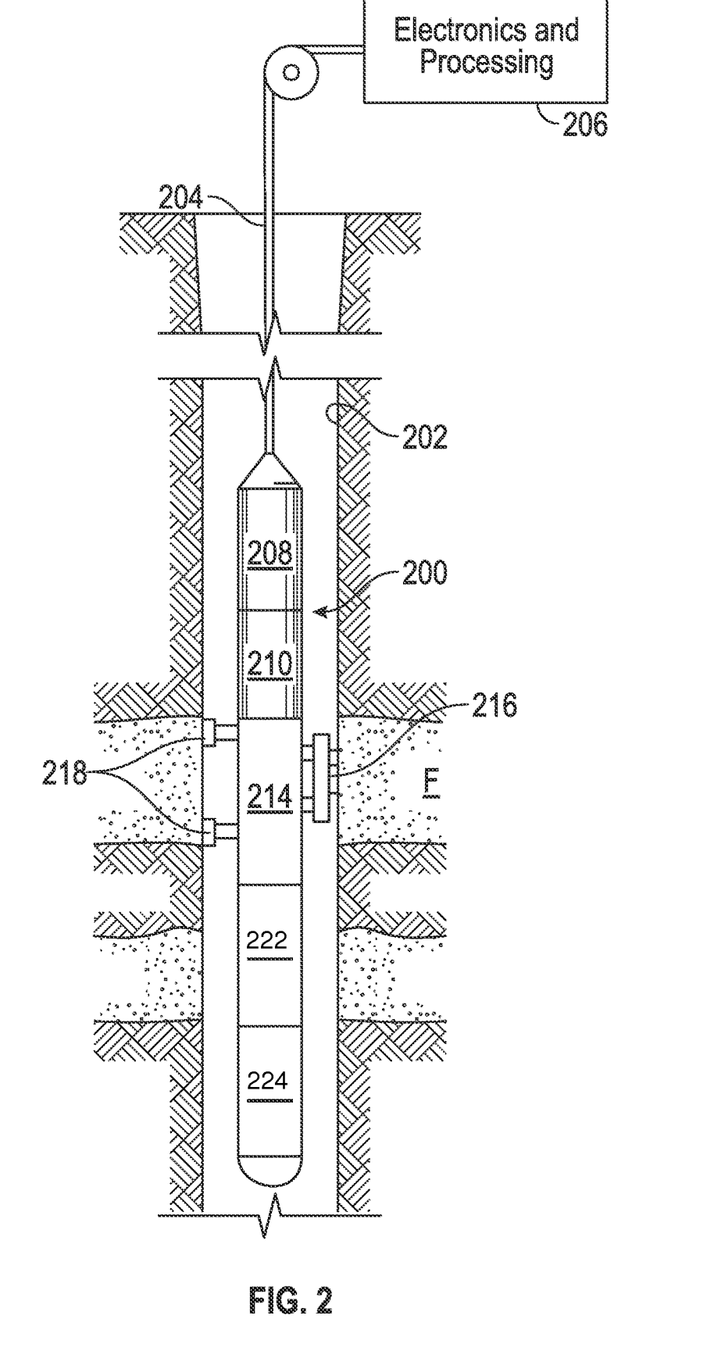
FIG. 2 is a schematic view of another embodiment of a wellsite system that may employ downhole fluid analysis methods for determining viscosity, according to aspects of the present disclosure.

FIGS. 1 and 2 depict examples of wellsite systems that may employ the fluid analysis systems and techniques described herein. FIG. 1 depicts a rig 100 with a downhole tool 102 suspended therefrom and into a wellbore 104 via a drill string 106. The downhole tool 100 has a drill bit 108 at its lower end thereof that is used to advance the downhole tool into the formation and form the wellbore. The drillstring 106 is rotated by a rotary table 110, energized by means not shown, which engages a kelly 112 at the upper end of the drillstring 106. The drillstring 106 is suspended from a hook 114, attached to a traveling block (also not shown), through the kelly 112 and a rotary swivel 116 that permits rotation of the drillstring 106 relative to the hook 114. The rig 100 is depicted as a land-based platform and derrick assembly used to form the wellbore 104 by rotary drilling. However, in other embodiments, the rig 100 may be an offshore platform.

Drilling fluid or mud 118 is stored in a pit 120 formed at the well site. A pump 122 delivers the drilling fluid 118 to the interior of the drillstring 106 via a port in the swivel 116, inducing the drilling fluid to flow downwardly through the drillstring 106 as indicated by a directional arrow 124. The drilling fluid exits the drillstring 106 via ports in the drill bit 108, and then circulates upwardly through the region between the outside of the drillstring and the wall of the wellbore, called the annulus, as indicated by directional arrows 126. The drilling fluid lubricates the drill bit 108 and carries formation cuttings up to the surface as it is returned to the pit 120 for recirculation.

The downhole tool 102, sometimes referred to as a bottom hole assembly ("BHA"), may be positioned near the drill bit 108 and includes various components with capabilities, such as measuring, processing, and storing information, as well as communicating with the surface. A telemetry device (not shown) also may be provided for communicating with a surface unit (not shown).

The downhole tool 102 further includes a sampling system 128 including a fluid communication module 130 and a sampling module 132. The modules may be housed in a drill collar for performing various formation evaluation functions, such as pressure testing and sampling, among others. According to certain embodiments, the sampling system 128 may be employed "while drilling," meaning that the sampling system 128 may be operated during breaks in operation of the mud pump 122 and/or during breaks in operation of the drill bit 108. As shown in FIG. 1, the fluid communication module 130 is positioned adjacent the sampling module 132; however the position of the fluid communication module 130, as well as other modules, may vary in other embodiments. Additional devices, such as pumps, gauges, sensor, monitors or other devices usable in downhole sampling and/or testing also may be provided. The additional devices may be incorporated into modules 130 and 132 or disposed within separate modules included within the sampling system 128.

The fluid communication module 130 includes a probe 134, which may be positioned in a stabilizer blade or rib 136. The probe 134 includes one or more inlets for receiving formation fluid and one or more flowlines (not shown) extending into the downhole tool for passing fluids through the tool. In certain embodiments, the probe 134 may include a single inlet designed to direct formation fluid into a flowline within the downhole tool. Further, in other embodiments, the probe may include multiple inlets that may, for example, be used for focused sampling. In these embodiments, the probe may be connected to a sampling flow line, as well as to guard flow lines. The probe 134 may be movable between extended and refracted positions for selectively engaging a wall of the wellbore 104 and acquiring fluid samples from the formation F. One or more setting pistons 138 may be provided to assist in positioning the fluid communication device against the wellbore wall.

FIG. 2 depicts an example of a wireline downhole tool 200 that may employ the systems and techniques described herein. The downhole tool 200 is suspended in a wellbore 202 from the lower end of a multi-conductor cable 204 that is spooled on a winch at the surface. The cable 204 is communicatively coupled to an electronics and processing system 206. The downhole tool 200 includes an elongated body 208 that houses modules 210, 212, 214, 222, and 224, that provide various functionalities including fluid sampling, fluid testing, operational control, and communication, among others. For example, the modules 210 and 212 may provide additional functionality such as fluid analysis, resistivity measurements, operational control, communications, coring, and/or imaging, among others.

As shown in FIG. 2, the module 214 is a fluid communication module 214 that has a selectively extendable probe 216 and backup pistons 218 that are arranged on opposite sides of the elongated body 208. The extendable probe 216 is configured to selectively seal off or isolate selected portions of the wall of the wellbore 202 to fluidly couple to the adjacent formation 220 and/or to draw fluid samples from the formation 220. The probe 216 may include a single inlet or multiple inlets designed for guarded or focused sampling. The formation fluid may be expelled to the wellbore through a port in the body 208 or the formation fluid may be sent to one or more fluid sampling modules 222 and 224. The fluid sampling modules 222 and 224 may include sample chambers that store the formation fluid. In the illustrated example, the electronics and processing system 206 and/or a downhole control system are configured to control the extendable probe assembly 216 and/or the drawing of a fluid sample from the formation 220.

Figure 3:
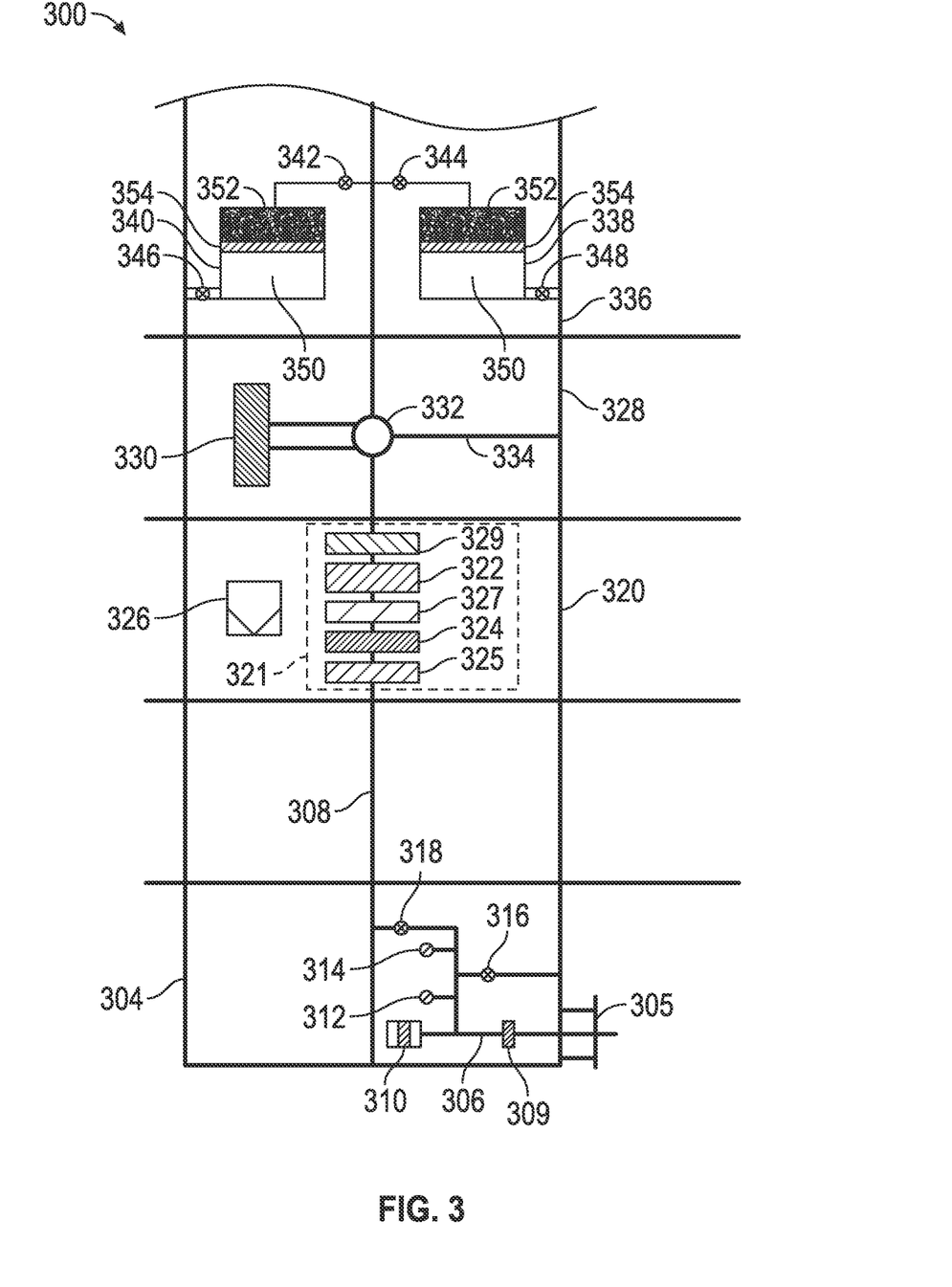
FIG. 3 is a schematic representation of an embodiment of a downhole tool that may employ downhole fluid analysis methods for determining viscosity, according to aspects of the present disclosure.

FIG. 3 is a schematic diagram of a portion of a downhole tool 300 that may employ the fluid analysis methods described herein. For example, the downhole tool 300 may be a drilling tool, such as the downhole tool 102 described above with respect to FIG. 1. Further, the downhole tool 300 may be a wireline tool, such as the downhole tool 200 described above with respect to FIG. 2. Further, in other embodiments, the downhole tool may be conveyed on wired drill pipe, a combination of wired drill pipe and wireline, or other suitable types of conveyance.

As shown in FIG. 3, the downhole tool 300 includes a fluid communication module 304 that has a probe 306 for directing formation fluid into the downhole tool 300. According to certain embodiments, the fluid communication module 304 may be similar to the fluid communication modules 130 and 214, described above with respect to FIGS. 1 and 2, respectively. The fluid communication module 304 includes a probe flowline 306 that directs the fluid to a primary flowline 308 that extends through the downhole tool 300. A resistivity sensor 309 may be disposed in the probe flowline 306 to measure the resistivity of the formation fluid. The fluid communication module 304 also includes a pump 310 and pressure gauges 312 and 314 that may be employed to conduct formation pressure tests. An equalization valve 316 may be opened to expose the flowline 306 to the pressure in the wellbore, which in turn may equalize the pressure within the downhole tool 300. Further, an isolation valve 318 may be closed to isolate the formation fluid within the flowline 306, and may be opened to direct the formation fluid from the probe flowline 306 to the primary flowline 308.

The primary flowline 308 directs the formation fluid through the downhole tool to a fluid analysis module 320 that includes a fluid analyzer 321 can be employed to provide in situ downhole fluid measurements. For example, the fluid analyzer 321 may include an optical spectrometer 322 and/or a gas analyzer 324 designed to measure properties such as, optical density, fluid density, fluid viscosity, fluid fluorescence, fluid composition, oil based mud (OBM), and the fluid gas oil ratio (GOR), among others. According to certain embodiments, the spectrometer 332 may include any suitable number of measurement channels for detecting different wavelengths, and may include a filter-array spectrometer or a grating spectrometer. For example, the spectrometer 332 may be a filter-array absorption spectrometer having ten measurement channels. In other embodiments, the spectrometer 322 may have sixteen channels or twenty channels, and may be provided as a filter-array spectrometer or a grating spectrometer, or a combination thereof (e.g., a dual spectrometer), by way of example. According to certain embodiments, the gas analyzer 324 may include one or more photodetector arrays that detect reflected light rays at certain angles of incidence. The gas analyzer 324 also may include a light source, such as a light emitting diode, a prism, such as a sapphire prism, and a polarizer, among other components. In certain embodiments, the gas analyzer 324 may include a gas detector and one or more fluorescence detectors designed to detect free gas bubbles and retrograde condensate liquid drop out.

One or more additional measurement devices 325, such as temperature sensors, pressure sensors, resistivity sensors, chemical sensors (e.g., for measuring pH or $H_2S$ levels), and gas chromatographs, may be included within the fluid analyzer 321. In certain embodiments, the measurement devices 325 may include a scattering detector that may be utilized to monitor phase separation, such as by detecting asphaltene, bubbles, oil mist from gas condensate, and/or other particles. The measurement devices 325 also may include a video imaging system that has a charge coupled device (CCD) or other type of camera. The imaging system may be used for spectral imaging to characterize phase behavior of fluids, such as monitoring asphaltene precipitation, bubble break out, and liquid separation from gas condensate, among others. Further, the fluid analyzer 321 may include a viscosity sensor 327, which for example, may be an x-ray sensor, micro NMR sensor, or a gamma ray sensor, among others, and a density sensor 329, which, for example, may be a densimeter or a densitometer. In other embodiments, the viscosity sensor and the density sensor may be combined into a single sensor, such as a microelectromechanical (MEMS) density and viscosity sensor or an ultrasonic transducer, that measures viscosity and density. In certain embodiments, the fluid analysis module 320 may include a controller 326, such as a microprocessor or control circuitry, designed to calculate certain fluid properties based on the sensor measurements. Further, in certain embodiments, the controller 326 may govern sampling operations based on the fluid measurements or properties. Moreover, in other embodiments, the controller 326 may be disposed within another module of the downhole tool 300.

The downhole tool 300 also includes a pump out module 328 that has a pump 330 designed to provide motive force to direct the fluid through the downhole tool 300. According to certain embodiments, the pump 330 may be a hydraulic displacement unit that receives fluid into alternating pump chambers. A valve block 332 may direct the fluid into and out of the alternating pump chambers. The valve block 332 also may direct the fluid exiting the pump 330 through the remainder of the primary flowline (e.g., towards the sample module 336) or may divert the fluid to the wellbore through an exit flowline 334.

The downhole tool 300 also includes one or more sample modules 336 designed to store samples of the formation fluid within sample chambers 338 and 340. The sample module 336 includes valves 342 and 344 that may be actuated to divert the formation fluid into the sample chambers 338 and 340. The sample chambers 338 and 340 also may include respective valves 346 and 348 that can be opened to expose a volume 350 of the sample chambers 338 and 340 to the annular pressure. In certain embodiments, the valve 346 or 348 may be opened to allow buffer fluid to exit the volume 350 to the wellbore, which may provide back-pressure during filling of a volume 352 that receives formation fluid. According to certain embodiments, the volume 352, which may store formation fluid, may be separated from the volume 350 by a floating piston 354.

The valve arrangements and module arrangements described herein are provided by way of example, and are not intended to be limiting. For example, the valves described herein may include valves of various types and configurations, such as ball valves, gate valves, solenoid valves, check valves, seal valves, two-way valves, three-way valves, four-way valves, and combinations thereof, among others. Further, in other embodiments, different arrangements of valves may be employed. For example, the valves 342 and 344 may be replaced by a single valve. Moreover, in certain embodiments, the respective positions of the modules 304, 320, 328, and 336 may vary. For example, in other embodiments, the fluid analysis module 320 may be disposed between the pump out module 328 and the sample module 336, rather than between the pump out module 328 and the probe module 304 as shown in FIG. 3. Moreover, other types of sample chambers, such as single phase sample bottles, among others, may be employed in one or more sample modules 336.

The downhole tools described above with respect to FIGS. 1-3 can be employed to collect formation fluid samples and measure properties of the fluid, such as optical density and the GOR, that can be used to determine viscosity at different vertical and/or lateral locations within a reservoir. According to certain embodiments, the viscosities can be employed to generate viscosity profiles of the reservoir, for example viscosity profiles for oil columns, and can also be interpreted to assess reservoir architecture. In certain embodiments, the optical density and GOR measurements may be employed to generate viscosity models that can be used to predict viscosities at other locations within the reservoir. The predicted viscosities may be compared to measured viscosities, such as those obtained by a viscosity sensor, and deviations from the predicted viscosities may indicate compartmentalization and/or disequilibrium within the reservoir. In certain embodiments, upon detecting compartmentalization and/or disequilibrium, the downhole tools may be moved to additional stations within the wellbore to take additional measurements for determining the reservoir architecture.

The viscosity models can be developed based on the relationship between the glass transition temperature ($T_g$) and viscosity ($\eta$). Dead heavy oil viscosity is related to glass temperature ($T_g$) as expressed below in Equation (1), and as described further in commonly assigned U.S. Patent Publication No. 2010/0043538 to Cheng et al., which is hereby incorporated by reference herein in its entirety.

$$\ln \eta = -0.5734 + 20.4095 \left(\frac{T}{T_g}\right)^{-3.3018} \quad (1)$$

Equation (1) may be rewritten as the following generalized expression:

$$\ln \frac{\eta}{\eta_0} = c \left(\frac{T_g}{T}\right)^{3.3018} \quad (2)$$

where T is the temperature of the fluid; $\eta$ is the viscosity of the fluid; $\eta_0$ is the viscosity at the reference state (e.g., $\eta_0$=0.5636 cp for dead heavy oil); and c is a coefficient (e.g., c=20.4095 for dead heavy oil).

As shown above, Equation (2) accounts for the effect of temperature on viscosity. However, to extend the above expression to live fluids (e.g., oil), the effects of GOR and pressure on viscosity also may be considered. The effects of GOR and pressure can be taken into account by developing an empirical relationship that describes the effects of GOR and pressure on viscosity. The empirical relationship may be developed using historical data, such as that stored in a PVT (pressure-volume-temperature) database. The PVT database may store the weight percentage, molecular weight, molar percentage, and specific gravity of single carbon number hydrocarbon components, as well as PVT properties (e.g., GOR, API gravities, formation volume factor (FVF), densities, and viscosities) for a large number of samples from different petroleum reservoirs throughout the world. For undersaturated oil where viscosity is inversely proportional to GOR$^{1/3}$, the GOR and pressure corrections can be applied to Equation 2 for live fluids as follows:

$$\ln\eta = \ln\eta_0 + c\left(\frac{T_g}{T}\right)^{3.3018} + \frac{1}{3}\ln\left(\frac{GOR_{ref}}{GOR}\right) + 1.392\times10^{-2}(P-P_{ref}) \quad (3)$$

where GOR is the GOR of the fluid at the temperature T and the pressure P; $GOR_{ref}$ is GOR of the fluid at the reference state; P is the pressure in MPa; and $P_{ref}$ is the pressure of the fluid at the reference state. The coefficient $1.392\times10^{-2}$, as well as the coefficient c, can be adjusted for different types of fluids accordingly, for example by multiple regression analysis on historical data.

Eq. (3) may then be modified to incorporate asphaltene properties of the fluid. The $T_g$ is linearly related to the weight fraction of polymer in a polymer solution. For heavy oil, asphaltenes are suspended in oil as asphaltene clusters, which have the biggest sizes of the three asphaltene forms (asphaltene molecules, nanoaggregates, and clusters), according to the modified Yen model of asphaltenes (also referred to as the Yen-Mullins model). Asphaltene concentration variations are large with depth. Thus, $T_g$ is assumed to vary with asphaltene concentration. As a result, a linear relationship exists between asphaltene concentration and $T_g$ for heavy oil. For heavy oil, $T_g$ can be expressed as:

$$T_g = a + bW_{asph} \quad (4)$$

where $W_{asph}$ is the weight fraction of asphaltene in heavy oil; and a and b are adjustable parameters.

Figure 4:
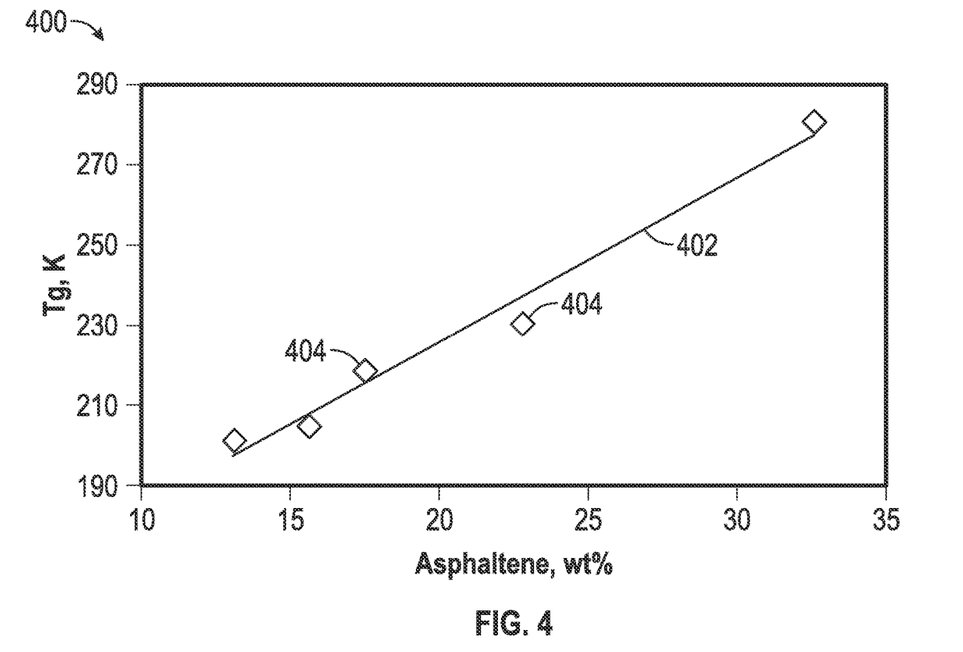
FIG. 4 is a chart demonstrating the linear correlation between asphaltene concentration and $T_g$ for heavy oil, according to aspects of the present disclosure.
Figure 5:
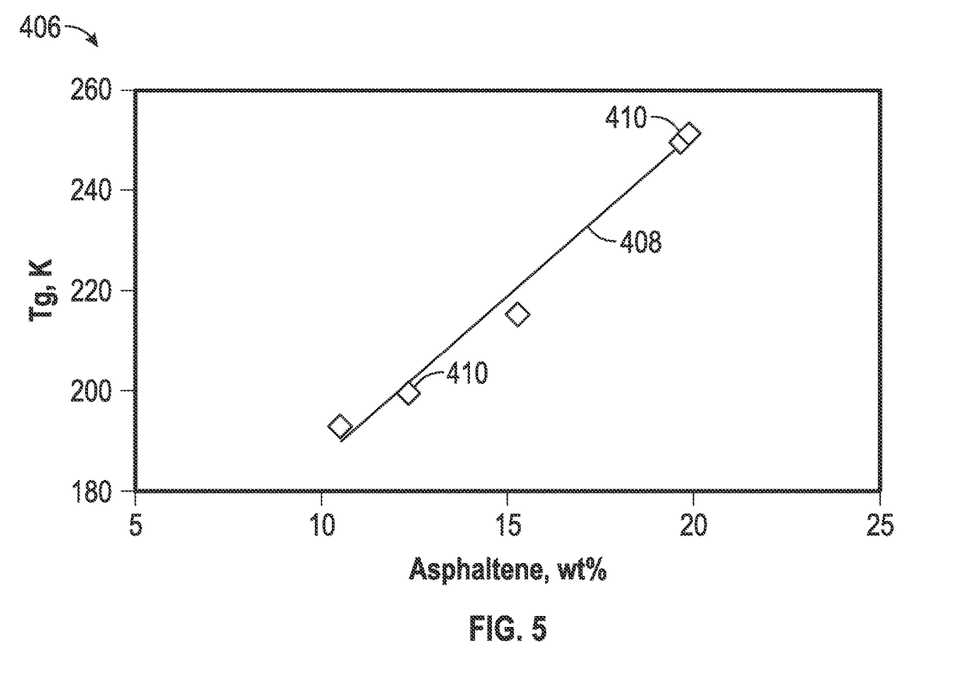
FIG. 5 is another chart demonstrating the linear correlation between asphaltene concentration and $T_g$ for heavy oil, according to aspects of the present disclosure.

FIGS. 4 and 5 demonstrate the linear correlation between asphaltene concentration and $T_g$ for heavy oil. In particular, FIG. 4 is a chart 400 depicting a linear correlation 402 between asphaltene weight percent, shown on the x-axis, and $T_g$, shown on the y-axis. The linear correlation 402 is a good fit for the individual data points 404, resulting from lab measurements of fluid samples. FIG. 5 is a chart 406 also depicting a linear correlation 408 between asphaltene weight percent, shown on the x-axis, and $T_g$, shown on the y-axis. The linear correlation 408 is a good fit for the individual data points 410, resulting from lab measurements of fluid samples.

Eq. (4) can be substituted into Eq. (3) for $T_g$, to produce the following relationship for heavy oil:

$$\ln\left(\frac{\eta}{\eta_0}\right) = c\left(\frac{a+bW_{asph}}{T}\right)^{3.3018} + \frac{1}{3}\ln\left(\frac{GOR_{ref}}{GOR}\right) + 1.392\times10^{-2}(P-P_{ref}) \quad (5)$$

According to the Yen-Mullins model of asphaltenes (e.g., the modified Yen model), asphaltenes have three forms in reservoir fluids: (1) Asphaltene molecules (e.g., with a size of ~1.5 nm) are dissolved in volatile oil at very low asphaltene content; (2) Asphaltene nanoaggregates (e.g., with a size of ~2 nm) are dispersed in stable crude oil at a bit higher asphaltene content; and (3) asphaltene clusters (e.g., with a size of ~5 nm) are found in mobile heavy oil at even higher asphaltene content (typically >5 wt % based on stock tank oil). The Yen-Mullins model has enabled the development of the Flory-Huggins-Zuo equation of state (FHZ EOS) for predicting asphaltene concentration gradients in oil reservoirs. The FHZ EOS is built by adding gravitational forces onto the existing the Flory-Huggins regular solution model that has been used to model the phase behavior of asphaltene precipitation in the oil and gas industry. For reservoir crude oils with a low gas/oil ratio (GOR), the FHZ EOS reduces predominantly to a simple form including the gravity term, and for mobile heavy oil, the gravity term simply utilizes asphaltene clusters. Additional details of the FHZ EOS can be found in the following commonly assigned patent publications, each of which are hereby incorporated herein by reference in their entirety: International Patent Publication WO2012/042397 to Zuo et al.; International Patent Publication WO2011/007268 to Zuo et al.; U.S. Pat. No. 7,996,154 to Zuo et al.; U.S. Pat. No. 8,271,248 to Pomerantz et al.; U.S. Pat. No. 7,822,554 to Zuo et al.; and U.S. Pat. No. 7,920,970 to Zuo et al.

Asphaltenes are dispersed in black oil as nanoaggregates and in light oil as molecules. In these cases, asphaltene concentrations are often relatively small (typically <5 wt %) and asphaltene gradients are relatively small compared to heavy oil. Further, $T_g$ slightly changes with asphaltene concentrations in black oil and light oil. Therefore, for black and light oils, Eq. (5) can be modified as follows:

$$\ln\left(\frac{\eta}{\eta_0}\right) = (c_1+c_2W_{asph})\left(\frac{T_g}{T}\right)^{3.3018} + \frac{1}{3}\ln\left(\frac{GOR_{ref}}{GOR}\right) + 1.392\times10^{-2}(P-P_{ref}) \quad (6)$$

where $T_g$ may be set to 246 K for black oils and light oils; and where $c_1$ and $c_2$ are adjustable parameters.

Asphaltene concentrations (e.g., weight fractions or percents) are linearly related to the optical density (OD) measured by downhole fluid analysis, as described above with respect to FIGS. 1-3. Therefore, viscosity may be calculated as by substituting optical density (OD) for the asphaltene concentrations ($W_{asph}$) 1 in Eqs. (5) and (6). For heavy oil, the asphaltene diameter obtained by the FHZ EOS is approximately 5 nm and the viscosity may be calculated by rewriting Eq. (5) as follows:

$$\ln\left(\frac{\eta}{\eta_0}\right) = c\left(\frac{a_1+b_1OD}{T}\right)^{3.3018} + \frac{1}{3}\ln\left(\frac{GOR_{ref}}{GOR}\right) + 1.392\times10^{-2}(P-P_{ref}) \quad (7)$$

where c is a coefficient (e.g., c=20.4095 for heavy oil); $\eta_0$ is the viscosity at the reference state (e.g., $\eta_0$=0.5636 cp); and $a_1$ and $b_1$ are adjustable parameters.

For black and light oils, the asphaltene diameter obtained by the FHZ EOS is approximately 1.5 nm for light oils or approximately 2 nm for black oils and the viscosity may be calculated by rewriting Eq. (6) as follows:

$$\ln\left(\frac{\eta}{\eta_0}\right) = (c_1 + c_2 OD)\left(\frac{T_g}{T}\right)^{3.3018} + \frac{1}{3}\ln\left(\frac{GOR_{ref}}{GOR}\right) + 1.392 \times 10^{-2}(P - P_{ref}) \quad (8)$$

where $\eta_0$ is the viscosity at the reference state (e.g., $\eta_0$=0.5636 cp); where $T_g$ is set to 246 K; and where $c_1$ and $c_2$ are adjustable parameters.

The adjustable parameters $c_1$, $c_2$, $a_1$ and $b_1$ may be determined by multiple regression analysis. For example, multiple measurements may be taken, either using historical values from the PVT database or by taking measurements at multiple stations within the wellbore, and multiple regressions analysis may be employed to determine the values for the adjustable parameters. Accordingly to certain embodiments, least squares regression analysis techniques, among others, may be employed.

Figure 6:
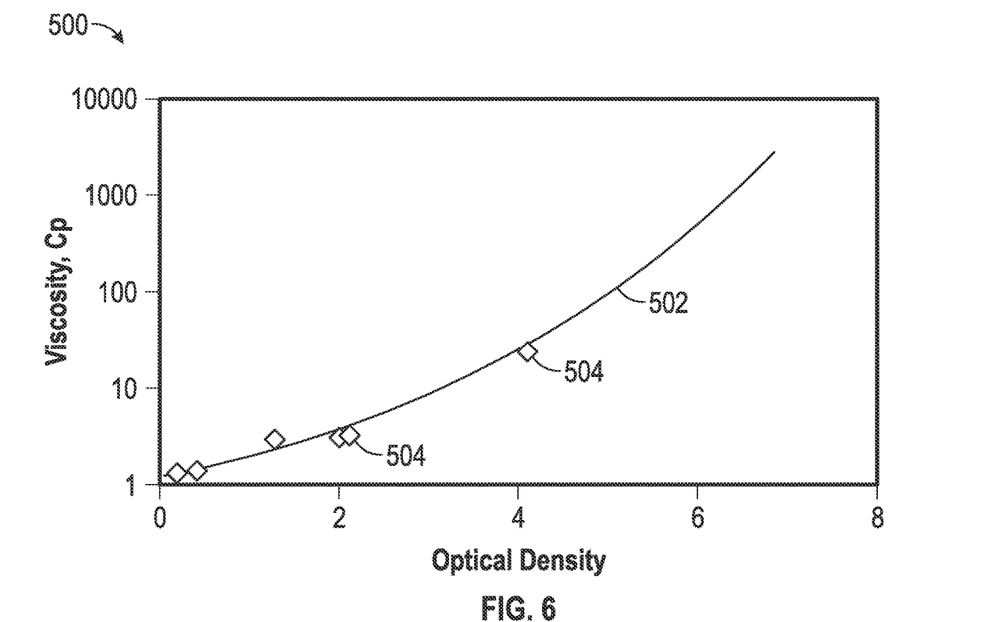
FIG. 6 is a chart depicting a viscosity profile determined using optical density, according to aspects of the present disclosure.
Figure 7:
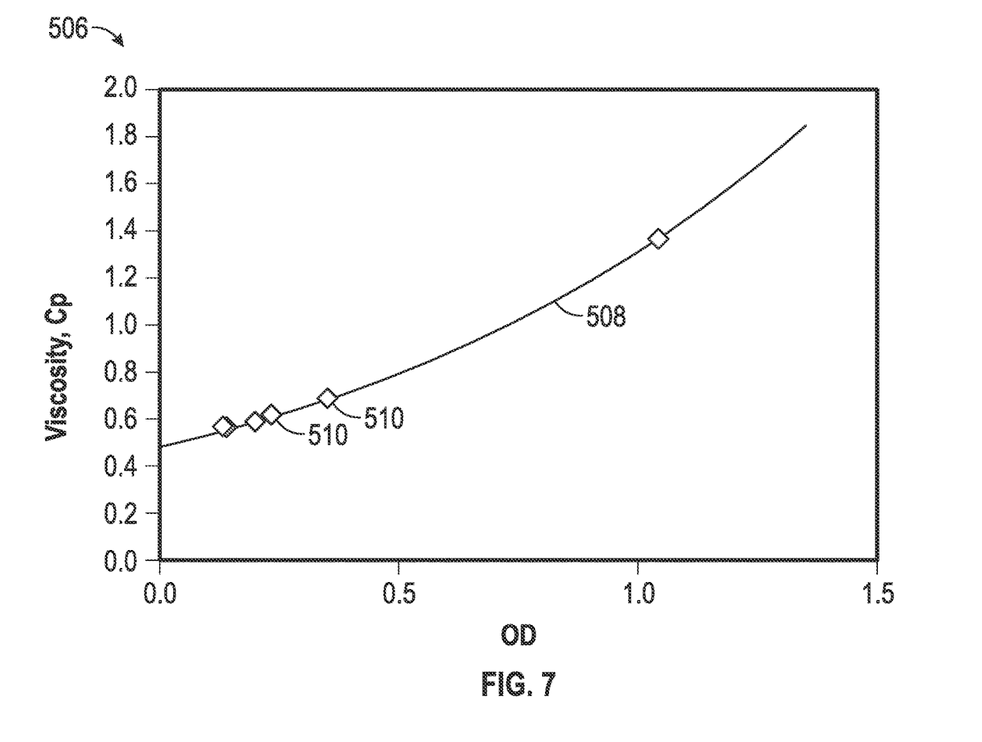
FIG. 7 is another chart depicting a viscosity profile determined using optical density, according to aspects of the present disclosure.

FIGS. 6 and 7 demonstrate the validity of Eqs. (7) and (8) for heavy oils and black and light oils, respectively. In particular, FIG. 6 is a chart 500 depicting a curve 502 representing the viscosity profile calculated using Eq. 7 where the OD is shown on the x-axis and the viscosity is shown on the y-axis. The curve 502 is a good fit for the individual data points 504, resulting from lab measurements of fluid samples. FIG. 7 is a chart 506 depicting a curve 508 representing the viscosity profile calculated using Eq. 8 where the OD is shown on the x-axis and the viscosity is shown on the y-axis. The curve 508 is a good fit for the individual data points 510, resulting from downhole measurements of fluid samples. It should be noted that Eq. (8) can also be used for heavy oil if $T_g$ is treated as an average value. For example, in a heavy oil reservoir, part of the oil is biodegraded but the other part is not. Therefore, the biodegraded and non-biodegraded oils have different $T_g$ and separate correlations may be used for the biodegraded and non-biodegraded oils.

Figure 8:
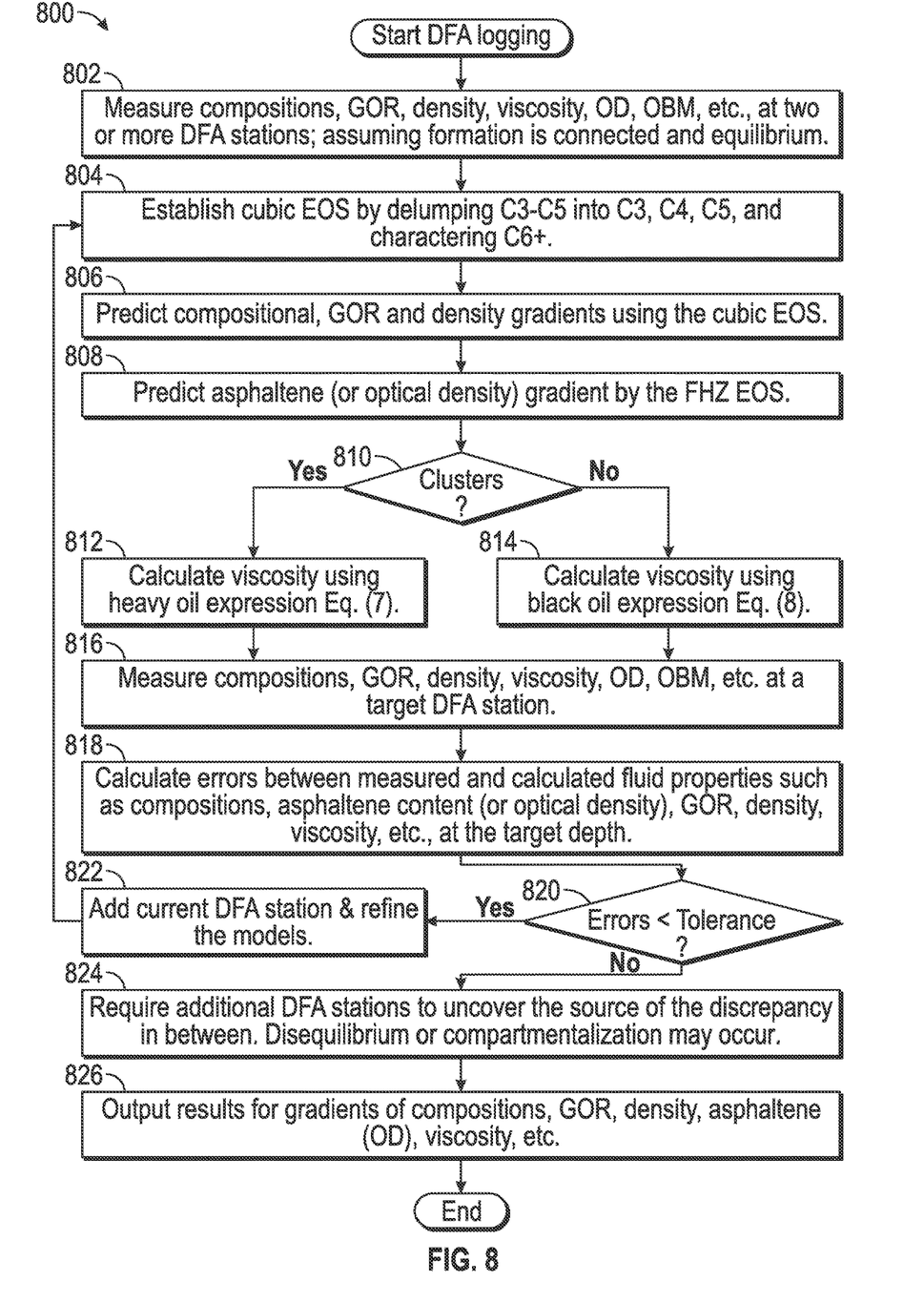
FIG. 8 is a flowchart depicting a method for assessing reservoir architecture using viscosity profiling, according to aspects of the present disclosure.

FIG. 8 is a flowchart depicting an embodiment of a method 800 that may be employed to assess reservoir architecture using the viscosity profiling techniques described herein. According to certain embodiments, the method 800 may be executed, in whole or in part, by the controller 326 (FIG. 3). For example, the controller 326 may execute code stored within circuitry of the controller 326, or within a separate memory or other tangible readable medium, to perform the method 800. In certain embodiments, the method 800 may be wholly executed while the tool 300 is disposed within a wellbore. Further, in certain embodiments, the controller 326 may operate in conjunction with a surface controller, such as the processing system 206 (FIG. 2), that may perform one or more operations of the method 800.

The method 400 may begin by analyzing (block 802) the formation fluid at stations within the wellbore. For example, the formation fluid may be withdrawn into the downhole tool 300 through the probe 305 and analyzed within the fluid analyzer 321, as described above with respect to FIG. 3. Formation fluid may be withdrawn into the downhole tool and analyzed at a first location in the wellbore. The downhole tool may then be moved to a second location in the borehole and formation fluid may then be withdrawn into the downhole tool and analyzed for the second location in the wellbore. In certain embodiments, the fluid analyzer 321 may measure the absorption spectra and translate the measurements into the concentrations of water ($H_2O$), carbon dioxide ($CO_2$), methane ($C_1$), ethane ($C_2H_6$), the $C_3$-$C_5$ alkane group including propane, butane, and pentane, and the lump of hexane and heavier alkane components ($C_6+$), among others. The fluid analyzer 321 may then employ the foregoing compositional information to determine additional fluid properties, such as the condensate yield and the gas-oil-ratio (GOR), among others. In certain embodiments, the controller 326 may operate in conjunction with the fluid analyzer 321 to determine the additional fluid properties using the composition information received from the fluid analyzer 321. The fluid analyzer 321 also may measure the density and viscosity of the fluid, for example, using the viscosity sensor 327 and the density sensor 329. Additional details of fluid analysis techniques and methods that may be employed to analyze (block 402) the formation fluid are described in the following commonly assigned U.S. Pat. No. 8,434,356 to Hsu et al.; U.S. Pat. No. 7,920,970 to Zuo et al.; U.S. Pat. No. 7,822,554 to Zuo et al.; U.S. Pat. No. 7,526,953 to Goodwin et al.; U.S. Pat. No. 6,476,384 to Mullins et al; U.S. Pat. No. 5,331,156 to Hines et al.; and U.S. Pat. No. 4,994,671 to Safinya et al.; which are each herein incorporated by reference in their entirety.

The method may then continue by establishing a cubic EOS model (block 804). The cubic EOS model may be developed by delumping the concentrations of carbon components measured by the fluid analyzer 321. Accordingly to certain embodiments, the fluid analyzer measures the individual concentrations of the methane, ethane and $CO_2$ and the lumped concentration of the $C_3$ through $C_5$ components (propane, butane, pentane and their isomers). The $C_3$ through $C_5$ composite concentration can then be split into the individual carbon component concentrations using a ratio rule or other empirical correlations known to those skilled in the art. For example, a ratio rule such as a 3:2:1 (or 4:3:2) ratio of $C_3$:$C_4$:$C_5$ can be employed where the $C_3$ through $C_5$ concentration is divided into 3 parts $C_3$ components, 2 parts $C_4$ components, and 1 part $C_5$ components. In other embodiments, the composite concentration may represent another range of carbon components, such as a $C_2$ through $C_4$ composite concentration, among others, that can be split into the individual carbon component concentrations.

The fluid analyzer 321 may also measure the composite concentration for the $C_6$-components. The $C_6$-components may be delumped to determine the composition of the formation fluid, broken down by each carbon number component. In certain embodiments, the controller 326 may execute algorithms that determine the composition of the formation fluid, broken down by each carbon number component rather than by the grouping of certain carbon components, based on an empirical relationship developed using a historical PVT database. The PVT database may store the weight percentage, molecular weight, molar percentage, and specific gravity of single carbon number alkane components, as well as PVT properties (e.g, GOR, API gravities, formation volume factor (FVF), densities, and viscosities) for a large number of samples from different petroleum reservoirs throughout the world. The weight percentage for each component (e.g., each carbon number component) may be derived based on the information from the fluid analyzer 321 and the empirical relation derived from analysis of the PVT database. Additional details of the delumping process are described in U.S. Pat. No. 7,920,970 to Zuo et al., previously incorporated by reference. The results of the delumping process provide the composition of the formation fluid, such as the mole or weight percentage for each carbon number component in the formation fluid. In certain embodiments, rather than employing a ratio rule as described in the preceeding paragraph, the delumping process also may be employed to determine the individual weight percentages of the carbon component numbers in the $C_3$-$C_5$ component group.

Delumping Process

An embodiment of the delumping process may employ a Pressure-Volume-Temperature (PVT) database to assist in determining the weight percentages of each carbon number component. The PVT database is a historical database that stores properties for a large number of samples from different petroleum reservoirs throughout the world. The properties are obtained by analyzing a large number of samples (e.g., 100 or more samples) collected from the different petroleum reservoirs. The properties include the weight percentage, molecular weight, molar percentage, and specific gravity for single carbon number alkane components included within the samples, as well as PVT properties such as the gas oil ratio (GOR), American Petroleum Institute (API) gravity, formation volume factor (FVF), density, and viscosity of the sample fluid.

The combined weight percentages for the component groups (e.g., the $C_3$-$C_5$ alkane group and the C6+ group, among others), can then be broken down into weight percentages for the individual single carbon number components within these groups using the PVT database. In particular, the weighting factors for each single carbon number component within a component group can be obtained by solving a formula (e.g., an empirical relation) that relates the weighting factor for each component to its carbon number. The formula is developed from the PVT database. For example, for the $C_3$-$C_5$ alkane group, the previously determined weight percentages for the single carbon number components (e.g., $C_3$, $C_4$, and $C_5$) within this group have been found to follow the linear equation $\psi_i = A*CN_i + B$ where $\psi_i$ is the weighting factor for each respective component (e.g., $C_3$, $C_4$, and $C_5$); $CN_i$ is the carbon number (e.g., 3, 4, or 5), and A and B are constants that can be solved for using regression over the weight percentages for the single carbon number components stored within the PVT database. The values of the constants may vary depending on the data included within the PVT database. After the constants have been determined, the formula can be used to determine the weighting factors for the single carbon number components within the $C_3$-$C_5$ alkane group included in the sample fluid. The weighting factors can then be normalized to determine the weight percentages. For example, the weighting factors may provide the relative amounts of the components within the group (e.g., the ratio between the components), and they may then be converted to weight percentages.

The weight percentage for another single carbon number component (e.g., the $C_6$ alkane component) can then be determined using one of the weight percentages from the $C_3$-$C_5$ alkane group. In particular, the weight percentage for the $C_6$ alkane component can be obtained by solving a formula (e.g., an empirical relation) that relates the weight percentage for the $C_6$ alkane component to the weight percentage of the $C_5$ alkane component. The formula is developed from the PVT database by determining a linear relationship between the $C_6$ weight percentages stored within the database and the $C_5$ weight percentages stored within the database. For example, the $C_6$ weight percentages have been round to follow the linear equation $W_{C6} = C*W_{C5}$ where C is a constant that can be solved for using linear regression over the weight percentages for the single carbon number components stored within the PVT database. The values of the constant may vary depending on the data included within the PVT database. In certain embodiments, the parameter C may fall within the range from 0.1 to 3. After the constant C has been determined, the formula can be used to determine the weight percentage of the $C_6$ alkane component in the sample fluid using the previously determined weight percentage of the $C_5$ component.

The weight percentage for the $C_{7+}$ group of components may then be determined by subtracting the weight percentage for $C_6$ from the weight percentage of the $C_{6+}$ group, measured by the fluid analyzer. The molecular weight for the $C_{7+}$ group of components can be calculated by solving a formula (e.g., an empirical relation) that relates the molecular weight to the GOR of the reservoir. The formula is developed from the PVT database. For example, for the $C_{7+}$ alkane group where the GOR of the reservoir is between 10 scf/stb and 10,000 sct/stb, the previously determined molecular weights stored within the PVT database have been found to follow the equation $MW = \alpha_1 * GOR^{\alpha_2}$ where $\alpha_1$ and $\alpha_2$ are constants that can be solved for using regression over the molecular weights and GOR values for the corresponding reservoirs stored within the PVT database. The values of the constants may vary depending on the data included within the PVT database. In certain embodiments, the parameter $\alpha_1$ is in the range between 500 and 1000 and the parameter $\alpha_2$ is in the range between −0.2 to 0.2. After the constants have been determined, the formula can be used to determine the molecular weight for the $C_{7+}$ alkane group.

In another example, for the $C_{7+}$ alkane group where the GOR of the reservoir is less than 10 scf/stb, the previously determined molecular weights stored within the PVT database have been found to follow the equation $MW = \beta_1 * GOR + \beta_2$ wherein $\beta_1$ and $\beta_2$ are constants that can be solved for using regression over the molecular weights and GOR values for the corresponding reservoirs stored within the PVT database. In certain embodiments, parameter $\beta_1$ is in the range between −10 to 10 and parameter $\beta_2$ is in the range between 0 and 1000. After the constants have been determined, the formula can be used to determine the molecular weight for the $C_{7+}$ alkane group.

The specific gravity of the $C_{7+}$ alkane group can then be determined using the molecular weight for the $C_{7-}$ alkane group. The specific gravity can be can be calculated by solving a formula (e.g., an empirical relation) that relates the molecular weight to the specific gravity. The formula is developed from the PVT database. For example, for the $C_{7+}$ alkane group, the previously determined molecular weights stored within the PVT database have been found to follow the equation $SG = \eta_1 \ln(MW) + \eta_2$ where $\eta_1$ and $\eta_2$ are constants that can be solved for using regression over the molecular weights and specific gravity values for the corresponding reservoirs stored within the PVT database. The values of the constants may vary depending on the data included within the PVT database. In certain embodiments, $\eta_1$, $\eta_2$ are each in the range between 0 and 0.3. After the constants have been determined, the formula can be used to determine the specific gravity for the $C_{7+}$ alkane group.

The weight percentages for single carbon number alkane components $C_7$ to $C_{max}$ are then determined. In certain embodiments, $C_{max}$ is in the range between $C_{45}$ and $C_{120}$. The weight percentages for the individual carbon components can be related to carbon number $C_i$ according to the following equations:

$$\ln W_{Ci} = D + E * CNi \quad (9)$$

$$\sum_{i=C7}^{Cmax} W_{Ci} = \sum_{i=C7}^{Cmax} D + E * CNi = W_{C7+} \quad (10)$$

$$\sum_{i=C7}^{Cmax} \frac{W_{Ci}}{MW_{Ci}} = \sum_{i=C7}^{Cmax} \frac{D + E * CNi}{MW_{Cj}} = \frac{W_{C7+}}{MW_{C7+}} \quad (11)$$

The parameters D and E can be derived by solving Equations (10) and (11). Having derived parameters D and E, the weight percentages for single carbon number alkane components C7 to Cmax can be derived from Equation (9).

The molecular weight (MW) for single carbon number alkane components $C_7$ to $C_{max}$ can then be determined. The molecular weight (MW) for the single carbon number alkane components $C_7$ to $C_{45}$ can be set from the values in the third column of Table 1 below. The molecular weight (MW) for the single carbon number alkane components beyond $C_{45}$ is given by the following equation:

$$MW_{Ci} = 14 CN_i - 4 \quad (12)$$

The specific gravities for single carbon number alkane components $C_7$ to $C_{max}$ are also determined. The specific gravities for the single carbon number alkane components $C_7$ to $C_{45}$ are listed in column 2 of Table 1 below.

TABLE 1

| Hydrocarbon Group | Specific Gravity | Molecular Weight (g/mol) |
|---|---|---|
| C7 | 0.722 | 96 |
| C8 | 0.745 | 107 |
| C9 | 0.764 | 121 |
| C10 | 0.778 | 134 |
| C11 | 0.789 | 147 |
| C12 | 0.800 | 161 |
| C13 | 0.811 | 175 |
| C14 | 0.822 | 190 |
| C15 | 0.832 | 206 |
| C16 | 0.839 | 222 |
| C17 | 0.847 | 237 |
| C18 | 0.852 | 251 |
| C19 | 0.857 | 263 |
| C20 | 0.862 | 275 |
| C21 | 0.867 | 291 |
| C22 | 0.872 | 305 |
| C23 | 0.877 | 318 |
| C24 | 0.881 | 331 |
| C25 | 0.885 | 345 |
| C26 | 0.889 | 359 |
| C27 | 0.893 | 374 |
| C28 | 0.896 | 388 |
| C29 | 0.899 | 402 |
| C30 | 0.902 | 416 |
| C31 | 0.906 | 430 |
| C32 | 0.909 | 444 |
| C33 | 0.912 | 458 |
| C34 | 0.914 | 472 |
| C35 | 0.917 | 486 |
| C36 | 0.919 | 500 |
| C37 | 0.922 | 514 |
| C38 | 0.924 | 528 |
| C39 | 0.926 | 542 |
| C40 | 0.928 | 556 |
| C41 | 0.930 | 570 |
| C42 | 0.931 | 584 |
| C43 | 0.933 | 598 |
| C44 | 0.935 | 612 |
| C45 | 0.937 | 626 |

The specific gravity (SG) for the single carbon number alkane components beyond $C_{45}$ is given by the following equation:

$$SG_{Ci} = D_1 \ln(MW_{Ci}) + D_2 \quad (13)$$

$$\sum_{i=C7}^{Cmax} \frac{W_{Ci}}{\sum_{j=C7}^{Cmax} \frac{W_{Cj}}{SG_{Cj}}} = \sum_{i=C7}^{Cmax} \frac{D + E * CNi}{\sum_{j=C7}^{Cmax} \frac{D + E * CNj}{D_1 \ln(MW_{Cj}) + D_2}} = SG_{C7+} \quad (14)$$

The known specific gravity and molecular weight for a single carbon number alkane component (such as the $C_6$ alkane component) can be used in Equation (13) along with Equation (14) to solve for $D_1$ and $D_2$. After solving for $D_1$ and $D_2$, the specific gravity (SG) for the single carbon number alkane components beyond $C_{45}$ is given by Equation (13).

The molar percentages (MP) of all components are derived from the previously determined weight percentages of these components and the previously determined molecular weights (MW) of these components. For example, the molar percentages (MP) of all components may be derived using Equation (15):

$$MP_{Ci} = \frac{\frac{W_{Ci}}{MW_{Ci}}}{\sum_{i=1}^{Max} \left( \frac{W_{Ci}}{MW_{Ci}} \right)} \quad (15)$$

EOS Model

The delumping results can then be employed to establish the cubic EOS model, which represents the phase behavior of the petroleum fluid in the reservoir. The EOS model includes a set of equations that represent the phase behavior of the compositional components of the reservoir fluid. The equations can be extended to relate to one or more particular applications as described below in more detail. The equations derived employ as input the weight percentages, the molecular weights, and the specific gravities for the single carbon number alkane components (or data based thereon), as derived above. According to certain embodiments, the EOS model may be developed by assuming that the reservoir is connected and at equilibrium.

The equations of the EOS model can take many forms. For example, they can be any one of many cubic EOS, as is well known. Such cubic EOS include van der Waals EOS (1873), Redlich-Kwong EOS (1949), Soave-Redlich Kwong EOS (1972), Peng-Robinson EOS (1976), Stryjek-Vera-Peng-Robinson EOS (1986), and Patel-Teja EOS (1982). Volume shift parameters can be employed as part of the cubic EOS in order to improve liquid density predictions, as is well known. Mixing rules (such as van der Waals mixing rule) can also be employed as part of the cubic EOS. A statistical associating fluid theory, SAFT-type, EOS can also be used, as is well known in the art. Tuning of the EOS model typically involves tuning volume translation parameters, binary interaction parameters, and/or critical properties of the components of the EOS model. An example of EOS tuning is described in Reyadh A. Almehaideb et al., "EOS tuning to model full field crude oil properties using multiple well fluid PVT analysis," *Journal of Petroleum*

Science and Engineering, Volume 26, Issues 1-4, pp. 291-300, 2000, incorporated herein by reference in its entirety. Additional details of establishing the cubic EOS model can be found in U.S. Pat. No. 7,920,970 to Zuo et al., previously incorporated by reference.

For example, the equations of the EOS model can be extended for particular application(s), such as one or more of the following:

i) PVT property prediction and/or simulation (e.g., prediction and/or simulation of fluid properties of the reservoir such as phase envelope, pressure-temperature (PT) flash, constant composition expansion (CCE), differential liberation (DL), constant volume depletion (CVD), separation, viscosity, oil and gas formation volume factors (FVF), and compressibility factor);

ii) compositional and property gradient prediction;

iii) gas hydrate formation prediction;

iv) wax precipitation prediction;

v) asphaltene precipitation prediction; and vi) scaling prediction.

The equations of the EOS model(s) for the various applications can be part of a commercially available software package, such as PVT Pro, dbrSOLIDS, and dbrHydrate, all fluid modeling software commercially available from DBR Technology Center, a division of Schlumberger Canada Limited, located in Edmonton, Alberta, Canada.

Examples of equations of EOS models for gas hydrate prediction are described in H. J. Ng et al., "The Measurement and Prediction of Hydrate Formation in Liquid Hydrocarbon-Water Systems," *Industrial & Engineering Chemistry Fundamentals*, 15, 293 (1976); H. J. Ng et al., "Hydrate Formation in Systems Containing Methane, Ethane, Propane, Carbon Dioxide or Hydrogen Sulfide in the Presence of Methanol," *Fluid Phase Equilibria*, 21, 145 (1985); H. J. Ng et al., "New Developments in the Measurement and Prediction of Hydrate Formation for Processing Needs," *International Conference on Natural Gas Hydrates, Annals of the New York Academy of Sciences*, Vol. 715, 450-462 (1994); J. Y. Zuo et al. "Representation of Hydrate Phase Equilibria in Aqueous Solutions of Methanol and Electrolytes Using an Equation of State," *Energy and Fuels*, 14, 19-24 (2000); and J. Y. Zuo et al., "A Thermodynamic Model for Gas Hydrates in the Presence of Salts and Methanol," *Chemical Engineering Communications*, 184, 175-192 (2001), incorporated herein by reference in their entireties.

Examples of equations of EOS models for wax precipitation prediction are described in J. Y. Zuo et al., "An improved thermodynamic model for wax precipitation from petroleum fluids," *Chemical Engineering Science*, 56, 6941 (2001); and J. Y. Zuo et al., "Wax Formation from Synthetic Oil Systems and Reservoir Fluids," 11*th International Conference on Properties and Phase Equilibria for Product and Process Design*, Crete, Greece, May 20-25, (2007), incorporated herein by reference in their entireties.

In the certain embodiments, the EOS model for wax precipitation employs a distribution of n-paraffin in crude oil. Two different methods can be used for this purpose, one for systems with experimental high temperature gas chromatography (HTGC) data and the other for systems without HTGC data. Note that HTGC allows for the direct detection and quantification of n-paraffins up to very high molecular weights (up to n-$C_{90}$). It can provide both the total n-paraffin content and its decay with carbon numbers/molecular weights. Therefore, the HTGC data are directly used to characterize n-paraffins. For systems without HTGC data, solvent precipitation programs such as UOP 46-85, available from UOP LLC of Des Plaines, Ill., USA, or any of its variants, are standard procedures that provide a good estimate of the total wax content of stock tank oil (STO). If no total wax content is available, a correlation is used to estimate it. The exponential decay ($\alpha$) of the n-paraffins in reservoir fluids is defined as the ratio between the mass fractions of two successive n-paraffins, $$\alpha = \frac{wC_n}{wC_{n-1}}.$$

In certain embodiments, $\alpha$ is set to 0.88 as a default value. The physical properties of n-paraffins and residue are calculated by different correlations well known in the art. The improved wax model is employed to predict thermodynamic wax appearance temperature (WAT) locus of a live oil fluid. In order to observe the sensitivity of WAT to the amount of wax precipitated in the fluid, a series of wax quality lines at fixed amount of precipitated wax are calculated using the improved wax model.

An example of equations of an EOS model for asphaltene precipitation prediction is described in J. Du et al., "A Thermodynamic Model for the Predictions of Asphaltene Precipitation," *Petroleum Science and Technology*, 22, 1023 (2004), incorporated herein by reference in its entirety. In certain embodiments, the equations of the EOS model are solved by a computer-implemented iteration scheme (e.g., Newton-Raphson iteration).

Gradient Prediction

Once the EOS model is defined, it can be used to predict (block 806) compositional, GOR, and density gradients, as described in U.S. Pat. No. 7,822,554 to Zuo et al., previously incorporated by reference. For example, the EOS model may be employed to predict fluid analysis measurements, such as pressure, temperature, API gravity, formation volume factor, density, and viscosity, among others. The predicted fluid analysis measurements may then be compared to the fluid analysis measurements obtained by the fluid analyzer 321 at multiple stations. A difference between the predicted measurements and the measurements obtained by the fluid analyzer 321 that exceeds a certain threshold may indicate that a gradient (e.g., a compositional gradient, GOR gradient, or density gradient, among others) exists between the stations.

The asphaltene gradient can then be predicted (block 808) using the FHZ EOS, as described in U.S. Patent Pub. No. 2009/0312997 to Freed et al., hereby incorporated herein by reference in its entirety. For example, the fluid analysis measurements obtained by the fluid analyzer 321 may be employed to determine the solubility parameter of the maltene, the mean volume of the maltene, and the density of the maltene at each station. Asphaltene equilibrium curves may then be generated based on a two component model or a first thermodynamic principle model, and the asphaltene parameters may be constrained based on the solubility or volume parameters. The asphaltene equilibrium curves may then be compared to the measured fluid properties and a difference that exceeds a certain threshold may indicate that an asphaltene gradient exists.

Asphaltene Clustering Prediction

The FHZ EOS can then be employed to determine (block 810) whether asphaltene clusters exist, as described further in U.S. Patent Pub. No. 2013/0112406 to Zuo et al., hereby incorporated herein by reference in its entirety. For example, the EOS model may be employed to generate a family of curves that predict the concentration of a particular solute part class (e.g., resins, asphaltene nanoaggregates, asphaltene clusters, and combinations thereof) as a function of depth. For each solute part class, the family of curves may be compared to the concentrations determined based on the fluid analyzer 321 measurements at each station. The best matching curve provides a concentration profile of asphaltene pseudocomponents (e.g., resins, asphaltene nanoaggregates, larger asphaltene clusters, and combinations thereof) and corresponding aggregate size of asphaltenes as a function of depth in the reservoir.

Viscosity Calculations

If asphaltene clusters exist, the viscosity can then be calculated (block 812) using the heavy oil Eq. (7). On the other hand, if clusters to do not exists, the viscosity can be calculated (block 814) using Eq. (8) for black oils and light oils. According to certain embodiments, regression analysis can be employed to determine the coefficients for Eqs. (7) and (8). For example, the viscosity values (e.g., measured by the viscosity sensor), the optical densities, the GORs, the pressures, and the temperatures, from multiple stations can be employed to determine the values for the coefficients. The data from one of the stations may be used as the reference state data. In other embodiments, the coefficients may be determined by using regression analysis based on values in the PVT database. Once the coefficients have been determined, Eqs. (7) and (8) may be used to predict the viscosity at additional stations.

The downhole tool may then be moved to another station within the wellbore to analyze formation fluid at that station. For example, the formation fluid may be withdrawn into the downhole tool 300 through the probe 305 and analyzed within the fluid analyzer 321, as described above with respect to FIG. 3. The temperature, pressure, GOR, and OD determined at that station may then be used in Eq. (7) or (8) to calculate the viscosity. The calculated viscosity may then be compared (block 818) to the measured viscosity at that station. For example, the viscosity may be measured using the viscosity sensor 327. In certain embodiments, other measured fluid properties, such as compositions, asphaltene content, optical density, GOR, and density may also be compared to predicted properties, such as properties that may be predicted using the FHZ EOS models.

If the difference between the measured properties and the predicted properties are within a certain tolerance (block 820), the data from the current station may be employed (block 822) to further refine the cubic EOS (block 804). On the other hand, if the measured properties and the predicted properties are outside of an expected tolerance, the downhole tool 300 may be moved to additional stations (block 824) to acquire additional formation fluid measurements. In certain embodiments, the lack of agreement between the measured properties and the predicted properties may indicate disequilibrium or compartmentalization within the reservoir. The additional formation fluid measurements may then be employed to assess the reservoir architecture and identify disequilibrium or compartmentalization. After identifying discrepancy sources, the finalized equations (e.g., Eqs. 7 and 8), EOS models, and FHZ EOS models, may be used to output (block 826) reservoir architecture properties, such as composition, GOR, density, asphaltene, OD, and viscosity gradients, among others.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A downhole fluid analysis method comprising:
withdrawing formation fluid into a downhole tool at a plurality of stations within a wellbore;
analyzing the formation fluid within a fluid analyzer of the downhole tool to determine properties of the formation fluid for the plurality of stations, the fluid analyzer comprising at least one of an optical spectrometer and a gas analyzer comprising a light source and a detector; and
measuring, via the at least one of the optical spectrometer and the gas analyzer, an optical density of the formation fluid and a gas oil ratio of the formation fluid;
measuring, via a temperature sensor coupled to the fluid analyzer, a temperature of the formation fluid;
measuring, via a pressure sensor coupled to the fluid analyzer, a pressure of the formation fluid;
developing, via a controller coupled to the fluid analyzer, and based on the determined properties of the formation fluid, a relationship for predicting viscosity from the measured optical density; and
calculating, via the controller, a viscosity using said relationship;
wherein developing comprises selecting, based on whether asphaltene clusters exist within the formation fluid, an equation for predicting viscosity, and wherein said equation is one of a heavy oil equation or a black oil equation;
wherein the heavy oil equation is $$\ln\left(\frac{\eta}{\eta_0}\right) = c\left(\frac{a_1 + b_1 OD}{T}\right)^{3.3018} + \frac{1}{3}\ln\left(\frac{GOR_{ref}}{GOR}\right) + 1.392 \times 10^{-2}(P - P_{ref})$$

wherein the black oil equation is $$\ln\left(\frac{\eta}{\eta_0}\right) = (c_1 + c_2 OD)\left(\frac{T_g}{T}\right)^{3.3018} + \frac{1}{3}\ln\left(\frac{GOR_{ref}}{GOR}\right) + 1.392 \times 10^{-2}(P - P_{ref})$$

wherein $\eta$ is the viscosity of the formation fluid, $\eta_0$ is the viscosity at a reference state, c is a coefficient, OD is the optical density of the formation fluid, GOR is the gas oil ratio of the formation fluid at temperature T and pressure P, $T_{ref}$ and $P_{ref}$ are respectively the temperature and pressure of the formation fluid at the reference state, and $a_1$, $b_1$, $c_1$, and $c_2$ are adjustable parameters determined during the developing.

2. The downhole fluid analysis method of claim 1, wherein analyzing comprises measuring an absorption spectra of the formation fluid.

3. The downhole fluid analysis method of claim 1, wherein analyzing comprises measuring a viscosity of the formation fluid.

4. The downhole fluid analysis method of claim 1, wherein analyzing comprises determining concentrations of components within the formation fluid.

5. The downhole fluid analysis method of claim 1, wherein developing comprises designating one of the plurality of stations as a reference station and employing the determined properties for the designated station as reference values within the relationship.

6. The downhole fluid analysis method of claim 1, comprising:
   withdrawing additional formation fluid into the downhole tool at an additional station within a wellbore;
   comparing a measured viscosity at the additional station to the predicted viscosity calculated using the relationship; and
   determining whether the measured viscosity and the predicted viscosity are within a tolerance of one another.

7. The downhole fluid analysis method of claim 6, comprising initiating withdrawal of further formation fluid at subsequent stations within the wellbore in response to determining that the measured viscosity and the predicted viscosity are outside of the tolerance.

8. The downhole fluid analysis method of claim 6, comprising employing the determined properties to refine an equation of state model in response to determining that the measured viscosity and the predicted viscosity are within the tolerance.

9. The downhole fluid analysis method of claim 1, comprising employing the developed relationship to assess an architecture of a reservoir containing the wellbore.

10. A downhole tool comprising:
    a fluid analyzer to determine properties of formation fluid for a plurality of stations within a wellbore, the fluid analyzer comprising at least one of an optical spectrometer and a gas analyzer comprising a light source and a detector; and
    a controller configured to execute instructions stored within the downhole tool to:
      determine, via the at least one of the optical spectrometer and the gas analyzer, an optical density of the formation fluid and a gas oil ratio of the formation fluid;
      measure, via a temperature sensor coupled to the fluid analyzer, a temperature of the formation fluid;
      measure, via a pressure sensor coupled to the fluid analyzer, a pressure of the formation fluid;
      determine whether clusters exist within the formation fluid based on the determined properties;
      develop, based on the determined properties of the formation fluid, a relationship for predicting viscosity from a measured optical density; and
      determine a predicted viscosity using said relationship,
    wherein developing comprises selecting, based on whether asphaltene clusters exist within the formation fluid, an equation for predicting viscosity, and wherein said equation is one of a heavy oil equation or a black oil equation,
    wherein the heavy oil equation is $$\ln\left(\frac{\eta}{\eta_0}\right) = c\left(\frac{a_1 + b_1 OD}{T}\right)^{3.3018} + \frac{1}{3}\ln\left(\frac{GOR_{ref}}{GOR}\right) + 1.392 \times 10^{-2}(P - P_{ref})$$

wherein the black oil equation is $$\ln\left(\frac{\eta}{\eta_0}\right) = (c_1 + c_2 OD)\left(\frac{T_g}{T}\right)^{3.3018} + \frac{1}{3}\ln\left(\frac{GOR_{ref}}{GOR}\right) + 1.392 \times 10^{-2}(P - P_{ref})$$

wherein $\eta$ is the viscosity of the formation fluid, $\eta_0$ is the viscosity at a reference state, c is a coefficient, OD is the optical density of the formation fluid, GOR is the gas oil ratio of the formation fluid at temperature T and pressure P, $T_{ref}$ and $P_{ref}$ are respectively the temperature and pressure of the formation fluid at the reference state, and $a_1$, $b_1$, $c_1$, and $c_2$ are adjustable parameters determined during the developing.

11. The downhole tool of claim 10, wherein the fluid analyzer comprises an optical spectrometer, or a gas chromatograph, or both.

12. The downhole tool of claim 10, wherein the fluid analyzer comprises a viscosity sensor for measuring a viscosity of the formation fluid, and wherein the controller is configured to execute the instructions to compare the measured viscosity to the predicted viscosity determined using the relationship.

13. The downhole tool of claim 10, further comprising a probe module configured to direct the formation fluid into the downhole tool.

* * * * *